US005379647A

United States Patent [19]
Sherwin

[11] Patent Number: 5,379,647
[45] Date of Patent: Jan. 10, 1995

[54] HOLE ELONGATION TESTING SYSTEM

[75] Inventor: Glen R. Sherwin, Brentwood, Tenn.

[73] Assignee: Avco Corporation, Providence, R.I.

[21] Appl. No.: 164,628

[22] Filed: Dec. 9, 1993

Related U.S. Application Data

[63] Continuation of Ser. No. 880,239, May 8, 1992, abandoned.

[51] Int. Cl.⁶ ............................................. G01N 3/08
[52] U.S. Cl. ..................................... 73/834; 73/826; 73/831; 33/787
[58] Field of Search ............... 73/831, 834, 787, 788, 73/789, 790, 818, 826, 828, 833; 33/787, 790

[56] References Cited

U.S. PATENT DOCUMENTS 4,706,387 11/1987 Wichorek ........................ 73/834

FOREIGN PATENT DOCUMENTS 219850 9/1986 Japan ........................... 73/826

Primary Examiner—Hezron E. Williams
Assistant Examiner—Mashmiya Ashraf
Attorney, Agent, or Firm—Perman & Green

[57] ABSTRACT

A system for testing and measuring hole elongation or deformation in a test article. The system includes a frame, a bearing member, and a referencing arm. The frame has a receiving area adapted to receive a portion of a test article. The bearing member is positionable into a hole of the test article. The referencing arm is movably connected to the frame and is adapted to signal the location of a portion of the test article relative to the bearing member. A distance measuring device is wholly supported on the frame and arm to allow the test article to be tested to catastrophic failure without risk of damaging the measuring device.

18 Claims, 2 Drawing Sheets

HOLE ELONGATION TESTING SYSTEM

This is a continuation of copending application Ser. No. 07/880,239 filed on May, 8, 1992 now abandoned.

BACKGROUND OF THE INVENTION b 1. Field of the Invention

The present invention relates to testing and measuring systems for article deformation and failure and, more particularly, to a system for testing and measuring elongation of a hole in a test article.

2. Prior Art

There exists in the prior art a deformation testing and measuring system known as an extensometer. The extensometer is generally adapted to put a test article under a tensile load to test and measure elongation or longitudinal deformation of the test article. The current use of an extensometer in bearing tests makes it very difficult to obtain consistent hole elongation measurements during the bearing test. The extensometer includes in its measurement elongation of the test article, sometimes a test coupon, and the test fixture between the extensometer attachment points. Extensometer slippage is also a problem during tests leading to erroneous measurements. The extensometer is always removed prior to catastrophic failure to preclude damage to the extensometer.

It is an objective of the present invention to provide a new and improved testing and measuring system.

SUMMARY OF THE INVENTION

In accordance with the embodiment of the present invention, an apparatus for measuring deformation of a test article is provided. The apparatus comprising a testing attachment and means for moving the testing attachment. The testing attachment has means for receiving a first portion of the test article, means for fixedly connecting the test article to a frame of the testing attachment, and means for measuring the distance between two locations of the test article in the means for receiving. The means for moving the testing attachment can move the testing attachment relative to a second portion of the test article to thereby deform the test article.

In accordance with another embodiment of the present invention, a hole elongation measuring device is provided comprising a frame, a bearing member, and a referencing arm. The frame has a receiving area adapted to at least partially receive a test article. The bearing member is positioned in the frame and positionable into a hole of the test article. The referencing arm is movably connected to the frame and is adapted to signal the location of a portion of the test article in the receiving area.

In accordance with one method of the present invention, a method of measuring hole elongation of a test article is provided comprising steps of connecting a first portion of the test article to a hole elongation fixture, the fixture having a bearing surface positioned in a hole of the test article, contact between the bearing surface and the test article at the hole being substantially the only longitudinal retainment of the test article with the fixture; and moving the fixture relative to a second portion of the test article to longitudinally deform the test article between the bearing surface and the second portion.

BRIEF DESCRIPTION OF THE DRAWINGS

The foregoing aspects and other features of the invention are explained in the following description, taken in connection with the accompanying drawings, wherein.

DETAILED DESCRIPTION OF THE INVENTION

Figure 1:
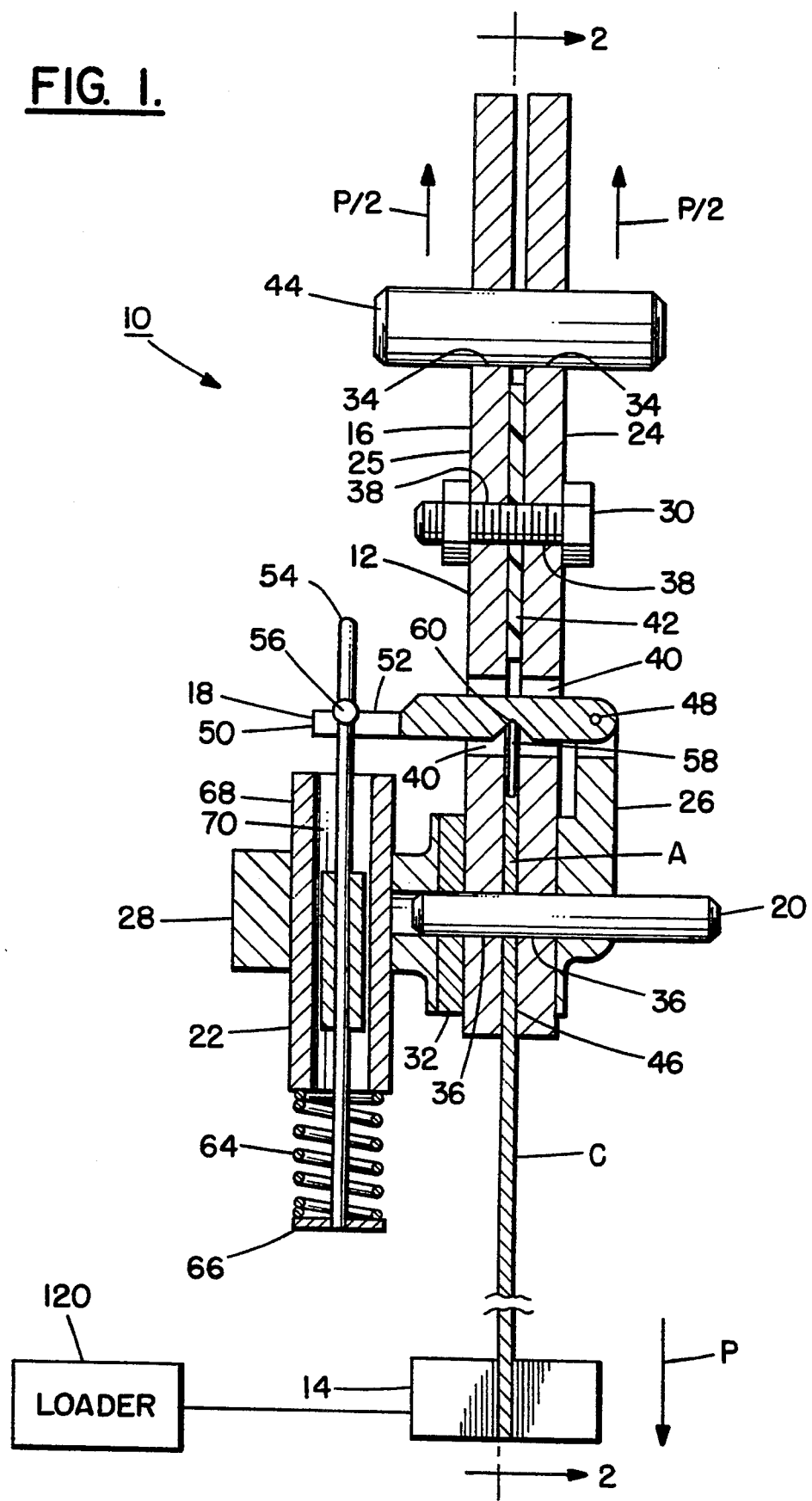
FIG. 1 is a schematic cross-sectional view of an apparatus for measuring deformation of a test article comprising features of the present invention.

Referring to FIG. 1, there is shown a schematic cross-sectional view of an apparatus 10 for measuring deformation of a test article C. Although the present invention will be described with reference to the embodiments shown in the drawings, it should be understood that the present invention can be embodied in many alternate forms of embodiments. In addition, any suitable size, shape, or type of elements or materials can be used as further understood from the description below.

The apparatus 10 generally comprises a testing attachment or fixture 12 adapted to be removably connected to a first end of the test article C, and a second end attachment 14 adapted to be removably connected to a second end of the test article C. A loader 120 is attached to the apparatus 10 to subject the coupon C to a longitudinal axial tension load. The second end attachment 14 and testing fixture 12 are moved relative to each other by the loader to thereby deform the coupon C. The testing fixture 12 generally comprises a frame 16, a referencing arm 18, a removable bearing pin 20, and a distance measurer 22. In the embodiment shown, the frame 16 generally comprises two plates 24 and 25, a pivot hinge bracket 26, a measuring device bracket 28, and a plate fastener 30. The pivot hinge bracket 26 is fixedly connected to the first plate 24. However, in an alternate embodiment, the bracket 26 may be integrally formed with the plate 24. The measuring device bracket 28 is fixedly connected to the second plate 25. However, in an alternate embodiment, the bracket 28 may be integrally formed with the second plate 25. In the embodiment shown, a shim 32 is provided between the bracket 28 and second plate 24 to help accommodate pin 20. However, the shim 32 need not be provided. The two plates 24, 25, in the embodiment shown, are identical to each other and, are connected to each other by the fastener 30. The fastener 30 merely comprises a nut and bolt. However, any suitable type of fastener could be provided. In addition, although plates 24, 25 are described as being removably fastened to each other, in an alternate embodiment only a section of the plates need be movable relative to each other in order to removably receive the first end A of the test article C (see FIG. 2). In the embodiment shown, each plate 24, 25 has a top bearing hole 34, a bottom bearing hole 36, a fastener hole 38, and a movable arm hole 40. The plates 24, 25 are connected to each other such that their respective holes are aligned. A shim 42 is located between the plates 24, 25 in order to obtain an appropriate spacing between the plates such that frictional forces between the plates and the upper end A of the test article C are eliminated, or at least substantially reduced. A load bearing pin 44 is located in the top bearing holes 34. The bearing pin 20 is adapted to be removably located in the bottom bearing holes 36 and across a test article receiving area 46 at the bottom of the plates 24, 25.

Figure 2:
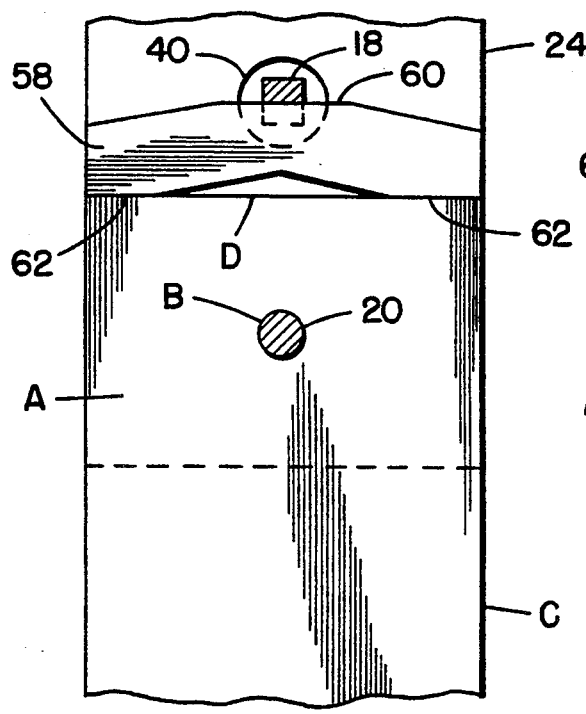
FIG. 2 is a partial cross-sectional view of the apparatus shown in FIG. 1 taken along line 2—2 prior to testing of the test article.

In the embodiment shown, the movable arm 18 is pivotally connected to the bracket 26 at pivot point 48. The arm 18 extends from the bracket 26, through the holes 40 in the plates, and out the opposite side. The arm 18, in the embodiment shown, has a "V" shaped notch on its bottom located at the junction of the two plates 24, 25. The end 50 of the arm, opposite the pivot point 48, includes two parallel projections 52 (only one of which is shown) with a space therebetween for receiving a portion of a movable measuring arm 54 of the distance measurer 22 therebetween. A pivot pin 56 is connected to arm 54 and rests in a seat on top of the parallel projections 52 to allow for pivotal movement between arm 18 and arm 54. Although the present invention has been described as having arm 18 being pivotally mounted to the frame 16 and connection of arm 18 to arm 54 as being pivotal, it should be understood that any suitable type of movable connection of arm 18 with plates 24, 25 and arm 54 can be provided. In the embodiment shown, the testing attachment 14 also comprises a pivot plate 58. As also seen in FIG. 2, the pivot plate 58 has a general inverted "V" shape with a top V-shaped edge 60 being located in the V-shaped bottom notch of the arm 18 and, two bottom spaced edge surfaces 62 adapted to contact the top edge D of the test article C. The pivot plate 58 is relatively free floating between the plates 24, 25, but is biased by the arm 18 against the top edge of the test article C. The arm 18 is biased against the pivot plate 58 by spring 64, plate 66, pin 56, and arm 54 of the measuring device 22.

The measuring device 22 comprises a housing 68 that is fixedly connected to the bracket 28 and, thus, is fixedly connected to the frame 16. The housing 68 has a center channel 70 which allows the measuring arm 54 to extend therethrough. The bottom of the measuring arm 54 is connected to the bottom plate 66. The spring 64 is compressed between the bottom of the housing 68 and the bottom plate 66 to bias the measuring arm 54 in a downward direction. Because the pin 56 rests on top of the arm 18, the arm 18 is thus biased in a downward direction. In the embodiment shown, the housing 68 and measuring arm 54 have suitable means, such as written indicia, that can be compared to indicate relative movement of the measuring arm 54 relative to the housing 68. Because the housing 68 is fixedly connected to the frame 16, the measuring arm 54 can thus indicate relative motion of the frame 16. Since the bearing pin 20 can be stationarily positioned in holes 36 in the frame 16 and, arm 18 is connected to measuring arm 54, the measuring arm 54 can thus indicate relative motion of the bottom spaced edge surfaces 62 of the pivot plate 58 relative to the bearing pin 20. Because the measuring device 22 is wholly contained on the frame 16, the test article C can be tested until catastrophic failure occurs without substantial risk of damage to the measuring device 22. Although a mechanical/optical measuring device has been described above, it should be understood that any suitable type of distance measuring device could be used.

Operation of the apparatus 10 is relatively simple and easy. A test article C, such as a test coupon, has its first end A positioned in the receiving area 46 and bearing pin 20 is inserted into the holes 36 of the frame 16 and hole B of the coupon C. The top edge D of the coupon C is contacted by the bottom surfaces 62 of the pivot plate 58. The coupon C is prevented from longitudinally moving relative to the frame 16 due merely to the positioning of bearing pin 20 in its hole B. From the initial setup or home position illustrated in FIGS. 1 and 2, the coupon C is then subjected to a longitudinal axial tension load. The load is applied at the second end attachment 14 with a force P and, an equal and opposite force is seen at the load bearing pin 44.

Figure 3:
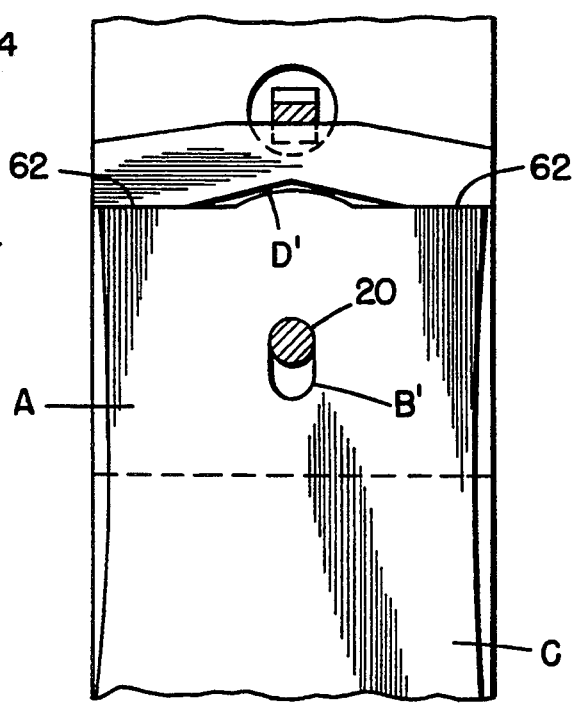
FIG. 3 is a view as in FIG. 3 wherein the test article has been deformed.

As can be seen with reference also to FIG. 3, when a sufficiently large enough load is applied to the coupon C, longitudinal elongate or deformation of the coupon C will occur. Even more precisely, because the coupon C is longitudinally retained with the testing fixture 12 merely due to the interlocking nature of the bearing pin 20 in hole B, the hole B becomes deformed or elongated as illustrated by B' in FIG. 3. The top D of the coupon C is also deformed or elongated as illustrated by D' in FIG. 3, while the free edges remains substantially undeformed. As can be seen by comparing FIGS. 2 and 3, the undeformed top edge D was substantially straight. However, the locally deformed top edge D' is now curved with the outer sections of the top edge, those contacted by bottom edge surfaces 62, being the least deformed from the original undeformed shape. This causes the pivot plate 58 to move downward in the receiving area 46 a distance equal to the hole elongation distance. Because pivot arm 18 is biased against the pivot plate 58, the arm 18 pivots downward and, measuring arm 54 is moved downward in the housing 68. The person testing the coupon C can then merely read the distance measurer 22 to obtain a measurement of the elongation or deformation of the coupon C at the hole B'.

Figure 4:
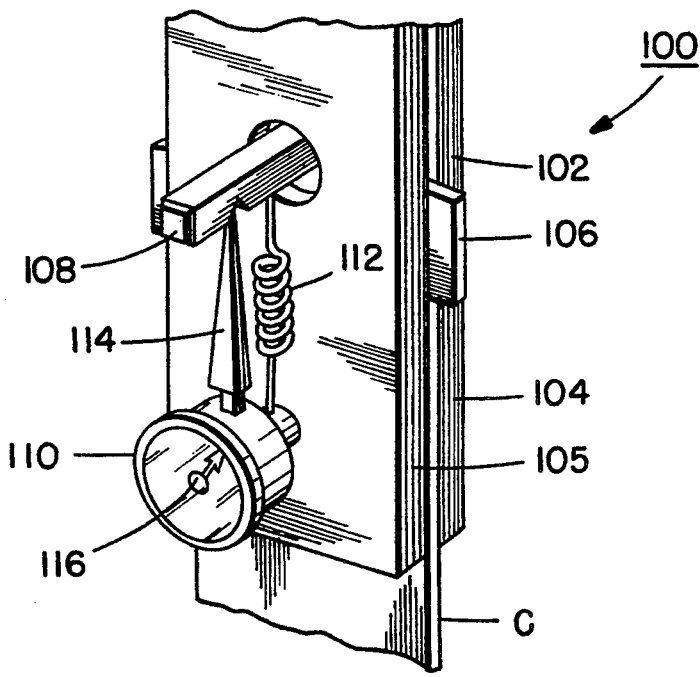
FIG. 4 is a partial perspective view of an alternate embodiment of the invention.

Referring now to FIG. 4, there is shown a partial perspective view of an alternate embodiment of the present invention. In the embodiment shown, the fixture 100 includes a frame 102 with two plates 104 and 105, a pivot plate 106, a pivot arm 108, a measuring device 110, and a loading spring 112. The loading spring 112 biases the pivot arm 108 downward against the pivot plate 106 and arm 114 of the measuring device 110. Movement of the pivot arm 108 will move the arm 114 and result in a reading at the dial indicator 116 of the measuring device 110. However, any suitable type of measuring system could be provided.

For the embodiments described above, the system is designed to measure hole elongation directly. It measures the displacement between the bearing pin and the free edge of the bearing coupon. The measuring device measures travel of the pivot arm which, due to the pivotal motion of the pivot arm and different contact locations on the pivot arm, can produce amplified displacement readings, such as three times the actual displacement, of the actual hole elongation in order to obtain more precise readings. The pivot arm rotation, preferably about 1°, makes the travel arc negligible and only linear travel is measured. The unique shape of the bottom of the pivot plate allows contact with the corner points of the coupon for the entire testing procedure. The present invention also allows the test coupon to be tested to catastrophic failure without damaging the fixture.

Let it be understood that the foregoing description is only illustrative of the invention. Various alternatives and modifications can be devised by those skilled in the art without departing from the spirit of the invention. Accordingly, the present invention is intended to embrace all such alternatives, modifications and variances which fall within the scope of the appended claims.

What is claimed is:

1. An apparatus for measuring deformation of a test article, the apparatus comprising:
   a testing attachment having means for receiving a first portion of the test article, means for fixedly connecting the test article to a frame of the testing attachment, and means for measuring the distance between two locations on the test article inside the means for receiving, the means for measuring including a first member for positioning in a hole of the test article inside the means for receiving and a second member for positioning on a top surface of the test article inside the means for receiving, the means for measuring measuring the distance between the first member and the top surface as the test article is deformed; and
   means for moving the testing attachment relative to a second portion of the test article to thereby deform the test article.

2. An apparatus as in claim 1 wherein the frame includes two plates adapted to sandwich the first portion of the test article therebetween.

3. An apparatus as in claim 1 wherein the means for measuring comprises an arm movably connected to the frame.

4. An apparatus as in claim 3 wherein the means for measuring includes a distance measuring device connected to the frame and the arm.

5. An apparatus as in claim 3 wherein the second member is a plate movably located between the arm and the test article.

6. An apparatus as in claim 4 wherein the distance measuring device includes a housing, a movable measuring arm, and a spring, biasing the measuring arm in a predetermined direction relative to the housing.

7. A hole elongation measuring device comprising:
   a frame having a receiving area adapted to at least partially receive a test article;
   a first bearing member positioned in the frame and positionable into a hole of the test article;
   a second bearing member positionable on a perimeter edge of the test article at two spaced corners of the perimeter edge inside the receiving area, the second bearing member being suitably sized and shaped relative to the test article such that the second bearing member initially contacts only the two spaced corners of the test article perimeter edge inside the receiving area; and
   a measurer connected to the first and second bearing members having a referencing arm movably connected to the frame, the arm extending into the receiving area and being adapted to signal the location of the second bearing member inside the receiving area to thereby signal the location of the two spaced corners of the perimeter edge of the test article relative to the hole of test article.

8. A device as in claim 7 wherein the second bearing member has two bottom spaced edge surfaces that are adapted to contact the two spaced corners of the test article, the perimeter edge being positionable in the frame perpendicular to an intended path of elongation of the test article.

9. A device as in claim 7 wherein the frame includes two spaced plates forming the receiving area therebetween.

10. A device as in claim 7 wherein the first bearing member is a removable pin.

11. A device as in claim 7 wherein the arm is pivotally connected to the frame.

12. A device as in claim 7 wherein the measurer includes a housing fixedly connected to the frame.

13. A device as in claim 12 wherein the measurer is wholly contained on the frame to allow the test article to be tested to catastrophic failure without substantial risk of damaging the measurer.

14. A method of measuring hole elongation of a test article, the method comprising steps of:
   connecting a first portion of the test article to a hole elongation fixture, the fixture having a bearing surface having a longitudinal axis, positioning the bearing surface; in a hole of the test article and the first portion being located in a receiving area of the hole elongation fixture, contact between the bearing surface and the test article at the hole being substantially the only longitudinal retainment of the test article with the fixture;
   positioning a member on a perimeter edge of the test article inside the receiving area, the perimeter edge being parallel to the longitudinal axis of the bearing surface;
   moving the fixture relative to a second portion of the test article to longitudinally deform the test article between the bearing surface and the second portion; and
   measuring a distance between the member on the perimeter edge of the test article and the bearing surface as the test article is being deformed.

15. A method as in claim 14 wherein the step of positioning comprises the member having two spaced edge surfaces that are positioned on outer corners of the perimeter edge, the two spaced edge surfaces initially comprising the only direct contact of the member with the test article.

16. A method as in claim 14 wherein the step of connecting comprises inserting a bearing pin into a hole in a frame of the fixture and the hole of the test article, the bearing pin forming the bearing surface.

17. A method as in claim 14 wherein the step of positioning positions the member on a top edge of the test article.

18. A method as in claim 14 wherein the step of measuring includes connecting a measuring arm to the member such that movement of the member moves the measuring arm.

* * * * *